United States Patent [19] [11] 4,303,650
Takezawa et al. [45] Dec. 1, 1981

[54] PROCESS FOR PRODUCTION OF ERYTHROPOIETIN

[75] Inventors: Kenji Takezawa, Yokohama; Hajime Hiratani, Osaka, both of Japan

[73] Assignees: Ajinomoto Co., Inc., Tokyo; Japan Chemical Research Co., Ltd., Kobe, both of Japan

[21] Appl. No.: 193,159

[22] Filed: Oct. 2, 1980

[30] Foreign Application Priority Data

Oct. 9, 1979 [JP] Japan .................................. 54-130677

[51] Int. Cl.³ ...................... A61K 37/00; A61K 35/22; C07G 7/00
[52] U.S. Cl. ................................. 424/177; 260/112 R; 424/99
[58] Field of Search .............. 424/99, 177; 260/112 R

[56] References Cited

U.S. PATENT DOCUMENTS 3,865,801 2/1975 Chiba et al. ........................... 424/99

OTHER PUBLICATIONS

Miyake et al.–The J. of Biol. Chem., vol. 252, Aug. 1977, pp. 5558–5564.
Espada et al.–Chem. Abst. vol. 73 (1970) p. 94956y.

Primary Examiner—Sam Rosen
Attorney, Agent, or Firm—Brisebois & Kruger

[57] ABSTRACT

The invention provides a novel process for the production of erythropoietin, which is a promising medicine for curing anemia, from human urine containing the same. The inventive method comprises adjusting the pH value of the urine in the range from 6 to 8, if the pH value of the urine is out of this range, and contacting the thus pH-controlled urine with a specific adsorbent so as that the erythropoietin is selectively adsorbed on the adsorbent. The adsorbed erythropoietin is then eluted out by use of an eluant solution to give the product in a partially purified form.

3 Claims, No Drawings

PROCESS FOR PRODUCTION OF ERYTHROPOIETIN

BACKGROUND OF THE INVENTION

The present invention relates to a process for the production of erythropoietin and, more particularly, to a method for the preparation of partially purified erythropoietin by separating from human urine by means of adsorption.

Erythropoietin is a hormone specifically stimulating erythropoiesis. It is an essential factor for the differentiation of hematopoietic stem cells into matured erythrocytes so that deficiency thereof causes anemia. Therefore, erythropoietin is a promising medicine for curing anemia or, in particular, renal anemia but unfortunately it is not in practical use due to its low availability.

Erythropoietin is a kind of protein so that, when it is intended to be used as a medicine, it is desirably to be prepared from a raw material of human origin in consideration of the possible antigenicity. As the starting raw material of human origin for the preparation of erythropoietin, there may be proposed, for example, human blood or urine from patients suffering from aplastic anemia or the like desease who excrete large amounts of erythropoietin in their urine. These raw materials are, however, limited in the quantity of supply. Accordingly, it will be the most advantageous way to develop a practical method for the preparation thereof from healthy human urine available in large volumes since much larger amounts can be expected as a total content of erythropoietin despite the low concentration thereof than with the above mentioned raw materials.

There have been hitherto made several attempts to obtain purified erythropoietin from human-origin raw materials. These attempts, however, are directed to the separation of erythropoietin from raw materials in small volumes, such as human blood or urine of anemic patients. These prior art methods are not suitable for treating large volumes of healthy human urine containing erythropoietin only in a low concentration with respect to the degree of concentration, yield of recovery, operability of the process and the production costs. A promising and practical way for separating erythropoietin from a large volume of human urine is an adsorption method with an adsorbent which is directly contacted with urine. No method in this way of direct adsorption has been proposed hitherto for treating not only urine from healthy human but also urine from anemic patients.

All of the adsorption methods hitherto proposed are preceded by a preliminary concentration or partial purification of erythropoietin by means of precipitation with a suitable precipitant or an organic solvent, salting out, dialysis and the like methods and the thus partially purified erythropoietin is adsorbed on an adsorbent such as, for example, anionic ion-exchange materials. The inventors have tried direct adsorption of erythropoietin on an adsorbent such as diethylaminoethylcellulose, strongly or weakly basic anionic ion-exchange resins and the like by directly contacting these adsorbents with human urine but without success since erythropoietin is scarcely adsorbed on these adsorbents.

SUMMARY OF THE INVENTION

It is therefore an object of the present invention to provide a novel and improved method for efficiently preparing erythropoietin from human urine.

It is another object of the present invention to provide an efficient and economical method for the production of partially purified erythropoietin preparation by use of a specific adsorbent which can adsorb selectively erythropoietin directly even from human urine.

Thus, the method of the present invention for the preparation of erythropoietin from human urine comprises (a) adjusting the pH value of the human urine in the range from 6 to 8, if the pH of the urine is out of this range, (b) contacting the human urine having the thus controlled pH value with an adsorbent selected from the group consisting of a polystyrene-based porous adsorbent resin, chitosan and diatomaceous earth whereby the erythropoietin is adsorbed on the adsorbent, (c) separating the adsorbent having adsorbed the erythropoietin from the depleted urine, and (d) eluting the adsorbed erythropoietin out of the adsorbent.

DETAILED DESCRIPTION OF THE PREFERRED EMBODIMENTS

The starting raw material of the inventive method is human urine.

The human urine may be used as such, or it may be waste urine after recovery of certain other valuable ingredients in small amounts such as urokinase and the like. Precipitates may be formed in human urine when the pH value of the urine is 7 or higher so that, though not essential, it is preferable that the human urine is first rendered weakly alkaline and the precipitates there formed are removed prior to adsorption. By this preliminary treatment, little of the erythropoietin is lost. The effectiveness of the inventive method is not affected essentially even without this preliminary treatment except for some inconveniences in the subsequent procedure.

Then the pH value of the urine is adjusted to 6 to 8 by the addition of a suitable inorganic or organic acid such as hydrochloric acid or an alkali such as sodium hydroxide and ammonia. When the pH value is outside this range, the adsorption of the erythropoietin is remarkably decreased.

The next step is the contacting of the urine having the thus controlled pH value with an adsorbent so as that the erythropoietin contained therein is efficiently and selectively adsorbed on the adsorbent. Suitable adsorbents are polystyrene-based porous adsorbent resins, chitosan and diatomaceous earth. The urine is passed through a column filled with the adsorbent or the urine is blended with a suitable amount of the adsorbent and agitated to suspend the adsorbent therein. The amount of the adsorbent to be used is determined depending on the types of the adsorbent and the content of the erythropoietin in the urine. Usually, an amount of 1 g or less of the adsorbent per 100 ml of the urine is sufficient. Therefore, the inventive method is economically very advantageous with the inexpensiveness of the above named adsorbents along with the high degree of concentration of the objective ingredient. In addition, these adsorbents exhibit behavoir of good dispersion and rapid precipitation when suspended in the urine so that the process of adsorption is greatly facilitated. By the use of this inventive method, practical production of erythropoietin from healthy human urine in large volumes can be successfully carried out. The adsorption of the erythropoietin on to the adsorbent is usually carried out at room temperature or below.

The adsorbent having adsorbed the erythropoietin is then separated from the depleted urine and subjected to elution. The method of the elution depends on the type of the adsorbent. For example, elution from the polystyrene-based porous adsorbent resin is carried out by using a eluant solution which may be an alcoholic solvent such as methyl alcohol, ethyl alcohol and the like, an aqueous alkaline solution or a mixture thereof. The elution from chitosan and diatomaceous earth is, on the other hand, carried out by using an aqueous alkaline solution containing sodium hydroxide, ammonia, sodium carbonate and the like.

Erythropoietin activity is determined with the exhypoxic polycythemic mouse assay proposed by P. M. Cotes (see P. M. Cotes and D. R. Bangham, Nature, volume 191 (1961), page 1065) if necessary, after concentration and dialysis, and the results are compared with the calibration curve (see L. Annable, P. M. Cotes and M. V. Mussett, Bulletin of World Health Organization, volume 47 (1972), page 99) prepared by use of the international reference preparation of erythropoietin (WHO Second International Reference Preparation of Erythropoietin, 67/343) and expressed in the international units (IU). Further, the specific activity, i.e. the ratio of the above determined IU value to mg of the protein content in the sample is determined with the content of the protein as determined by the biuret method with purified bovine serum albumin as the reference (see A. G. Gornall, C. S. Bardawill and M. M. David, Journal of Biological Chemistry, volume 177 (1949), page 751).

In the following, the method of the present invention is illustrated in further detail by way of examples.

EXAMPLE 1

The pH value of 10 liters of pooled urine of healthy human male was adjusted to 8.50 by adding small volumes of a 2N sodium hydroxide solution whereupon precipitates were formed in the urine. The total content of erythropoietin in the urine was 14.9 IU. After removal of the precipitates by decantation, the pH value of the urine was brought to 7.1 by adding 2N hydrochloric acid and 100 g of a polystyrene-based porous adsorbent resin (Amberlite XAD-7, a product by Rohm & Haas Co.) were added thereto. After 1.5 hours of agitation at room temperature, the supernatant was discarded by decantation to collect the resin. The content of the erythropoietin in the discarded liquid was less than 1.0 IU so that more than 93% of the erythropoietin in the original urine had been adsorbed on the resin.

The above obtained resin having adsorbed the erythropoietin was dispersed in 400 ml of a 0.01M tris buffer solution at pH 9.24 containing 80% by volume of ethyl alcohol and agitated for 3 hours at 7° C. Filtration of the above suspension gave an eluate solution which contained 13.6 IU of erythropoietin giving a recovery of about 91%. The specific activity (IU/mg protein) of this eluate solution was found to be increased to 6.1 times the value in the original urine.

It was calculated that 90.3% of erythropoietin remained in the urine after removal of the precipitates formed in the pretreatment with a pH of 8.50.

For comparison, the same procedure as above was repeated except that the pH value of the urine contacted with the adsorbent was 5.72 instead of 7.1 to find that only 23% of the erythropoietin was adsorbed on the adsorbent.

EXAMPLE 2

The pH value of 10 liters of pooled urine of healthy human male containing 7.50 IU of erythropoietin was adjusted to 8.50 by adding 2N sodium hydroxide solution and the precipitates formed there were removed by decantation. After bringing the pH value of the urine to 7.0 by adding 2N hydrochloric acid, the urine was admixed with 87 g of chitosan (FLONAC-N, a product by Kyowa Yushi Kogyo Co.) and agitated for 1.5 hours at room temperature. The supernatant was discarded by decantation to collect the chitosan.

The chitosan having adsorbed the erythropoietin was dispersed in 800 ml of a 0.1M sodium carbonate buffer solution at pH 11.00 containing 0.5M sodium chloride and agitated for 3 hours at 7° C. followed by filtration to give an eluate. The content of erythropoietin in this eluate was 5.93 IU giving a recovery of 79%. The specific activity (IU/mg protein) in the above eluate was found to be increased to 14.6 times the value in the original urine.

For comparison, the same procedure was repeated except that the pH value of the urine in contact with the chitosan was 5.98 instead of 7.0 to find that the recovery of erythropoietin was only 48%.

EXAMPLE 3

The pH value of 10 liters of pooled urine of healthy human male containing 11.2 IU of erythropoietin was adjusted to 8.50 by adding 2N sodium hydroxide solution and the precipitates formed there were removed by decantation. After the pH value was brought to 7.00 by adding 2N hydrochloric acid, the urine was admixed with 100 g of a diatomaceous earth (Hyflo Super-Cel, a product by Johns-Manville Corp.) and agitated for 35 minutes at room temperature. The supernatant was discarded by decantation to collect the diatomaceous earth.

The diatomaceous earth having adsorbed the erythropoietin was dispersed in 400 ml of a 4% ammonia water at pH 12.3 and agitated for 35 minutes at 7° C. followed by filtration to give an eluate. The content of the erythropoietin in this eluate was 5.69 IU giving a recovery of 50.8%. The specific activity (IU/mg of protein) in this eluate solution was found to be increased to 12.7 times the value in the urine.

For comparison, the same procedure as above was repeated except that the pH value of the urine in contact with the diatomaceous earth was 4.30 instead of 7.00 to find that the recovery of the erythropoietin was only 9.7%.

What is claimed is:

1. A process for the production of purified erythropoietin from human urine which comprises the steps of
(a) adjusting the value of pH of the urine in the range from 6 to 8, if the pH of the urine is out of this range,
(b) contacting the urine having the thus controlled pH value with an adsorbent selected from the group consisting of a polystyrene-based porous adsorbent resin, chitosan and diatomaceous earth whereby the erythropoietin is adsorbed on the adsorbent, (c) separating the adsorbent having adsorbed the erythropoietin from the depleted urine, and (d) eluting the erythropoietin out of the adsorbent.

2. The method as claimed in claim 1 wherein the step (a) is preceded by the steps of bringing the pH value of the urine to 7 or higher whereby impurity precipitates are formed in the urine and removing the precipitates from the urine.

3. The method as claimed in claim 1 wherein the step (d) is carried out using an aqueous alkaline solution as an eluant solution.

* * * * *